United States Patent
Takeuchi et al.

(10) Patent No.: US 7,898,154 B2
(45) Date of Patent: Mar. 1, 2011

(54) ULTRASOUND PROBE AND METHOD FOR MANUFACTURING THE SAME

(75) Inventors: Takashi Takeuchi, Otawara (JP); Takashi Ogawa, Nasushiobara (JP); Koichi Shibamoto, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 745 days.

(21) Appl. No.: 11/564,562

(22) Filed: Nov. 29, 2006

(65) Prior Publication Data

US 2007/0167807 A1     Jul. 19, 2007

(30) Foreign Application Priority Data

Nov. 30, 2005  (JP) .............................. 2005-347173

(51) Int. Cl.
  *H04R 17/00*  (2006.01)
(52) U.S. Cl. .................. 310/334; 367/155; 367/157; 600/437; 600/459
(58) Field of Classification Search .................. 310/334; 367/155, 157; 600/437, 459
  See application file for complete search history.

(56) References Cited

U.S. PATENT DOCUMENTS

| | | | | |
|---|---|---|---|---|
| 4,616,152 A | * | 10/1986 | Saito et al. | 310/334 |
| 5,115,809 A | * | 5/1992 | Saitoh et al. | 600/459 |
| 6,558,332 B1 | * | 5/2003 | Shimizu | 600/459 |
| 7,572,224 B2 | * | 8/2009 | Hosono et al. | 600/459 |
| 2001/0021807 A1 | * | 9/2001 | Saito et al. | 600/437 |
| 2001/0041837 A1 | * | 11/2001 | Takeuchi et al. | 600/437 |

FOREIGN PATENT DOCUMENTS

| | | |
|---|---|---|
| CN | 1755357 A | 4/2006 |
| JP | 4-347146 | 12/1992 |

* cited by examiner

*Primary Examiner*—Thomas M Dougherty
*Assistant Examiner*—Bryan P Gordon
(74) *Attorney, Agent, or Firm*—Oblon, Spivak, McClelland, Maier & Neustadt, L.L.P.

(57) ABSTRACT

In an ultrasound probe including first and second acoustic matching layers between an acoustic lens and a piezoelectric oscillator, an electrode is arranged on a surface of a laminate element made of the first and second acoustic matching layers, the laminate element is interposed between the acoustic lens and the piezoelectric oscillator, and the piezoelectric oscillator and the electrode are electrically connected.

12 Claims, 4 Drawing Sheets

ULTRASOUND PROBE AND METHOD FOR MANUFACTURING THE SAME

CROSS-REFERENCE TO RELATED APPLICATIONS

This application is based upon and claims the benefit of priority from prior Japanese Patent Application No. 2005-347173, filed Nov. 30, 2005, the entire contents of which are incorporated herein by reference.

BACKGROUND OF THE INVENTION

1. Field of the Invention

The present invention relates to an ultrasound probe and a method for manufacturing the ultrasound probe for use in an ultrasound diagnostic apparatus or an ultrasound probe device.

2. Description of the Related Art

An ultrasound probe is a device for transmitting a ultrasound to an object, and then, receiving a reflection wave from an interface having its different acoustic impedances in an object, thereby imaging an inside of the object. Such an ultrasound probe is used for an ultrasound diagnostic apparatus for examining an inside of a human body or an ultrasound probe device or the like for examining an inside of a structure.

Now, a description will be given with respect to an ultrasound probe for use in an ultrasound diagnostic apparatus.

FIG. 4 is a schematic view showing a configuration of a conventional ultrasound probe.

As shown in FIG. 4, this ultrasound probe has a casing 100 gripped by an operator. This casing 100 is formed in a rectangular cylinder shape, and an ultrasound transducer 101 is housed inside the casing.

The ultrasound transducer 101 comprises: a backing member 102; a signal substrate 103; a piezoelectric oscillator 104; a first acoustic matching layer 105; a second acoustic matching layer 106; a GND common electrode 107; and an acoustic lens 108 sequentially from the operator's frontal side. Among them, the signal substrate 103, the piezoelectric oscillator 104, the first acoustic matching layer 105, and the second acoustic matching layer 106 are arrayed with respect to a scanning direction (direction vertical to paper face).

The piezoelectric oscillator 104 generates and detects an ultrasound, and is composed of a piezoelectric material 104a, a GND electrode 104b, and a signal electrode 104c.

The first acoustic matching layers 105 and the second acoustic matching layers 106 match the acoustic impedances of the piezoelectric oscillator 104 and a subject. On surfaces of each of these layers, electrodes 105a and 106a are formed by means of sputtering, plating and the like. The electrodes 105a and 106a are so called electrode-drawing electrodes and electrically connect the GND electrode 104a of the piezoelectric oscillator 104 to the GND common electrode 107 with each other.

The GND common electrode 107 is made of a sheet shaped metal plate, and commonly uses the electrodes 106a of the second acoustic matching layers 106 divided by arraying.

The acoustic lens 108 enhances resolution of an ultrasound, and slightly protrudes from a distal end aperture portion 100a of the casing 100.

The signal substrate 103 is made of part of a flexible substrate 109, and provides a drive signal to each of the elements of the piezoelectric oscillator 104 divided by arraying.

The GND electrode 104b of the piezoelectric oscillator 104 is electrically connected to a control unit 110 via the electrodes 105a and 106a; the GND common electrode 107; and the flexible substrate 109. In addition, the signal electrode 104c of the piezoelectric oscillator 104 is electrically connected to the control unit 110 via the signal substrate 103 and the flexible substrate 109 (refer to Jpn. Pat. Appln. KOKAI Publication No. 4-347146, for example).

In the case of manufacturing the thus configured ultrasound transducer, the piezoelectric oscillator 104, the first acoustic matching layer 105, and the second acoustic matching layer 106 that have been reshaped in their required sizes and dimensions by means of dicing or the like are prepared, and then, the first and second acoustic matching layers 105 and 106 are sequentially adhered on the GND electrode 104b of the piezoelectric oscillator 104. Then, the signal substrate 103 and the backing member 102 are sequentially adhered on the signal electrode 104c of the piezoelectric oscillator 104, and then, a laminate element composed of these piezoelectric oscillator 104, first and second acoustic matching layers 105 and 106, and signal substrate 103 is arrayed with respect to a scanning direction. Then, the GND common electrode 107 and the acoustic lens 108 are sequentially adhered on the second acoustic matching layers 106, and then, the control unit 110 is electrically connected via the flexible substrate 109. In this manner, an ultrasound transducer 101 is completed.

However, in a conventional ultrasound probe manufacturing method, when the ultrasound transducer has been completed, displacement has sometimes occurred between the piezoelectric oscillator 104 and the first acoustic matching layer 105 or between the first acoustic matching layer 105 and the second acoustic matching layer 106. Therefore, in order to prevent ultrasound transducer 101 from disabling entry into the casing 100 due to this displacement, a margin M is provided in advance to dimensions of the casing 100.

However, there has been a problem that, if the margin M is provided to the dimensions of the casing 100, a subject's contact portion S of the ultrasound probe, i.e., a portion that comes into contact with a subject increases in size, and, when a narrow portion such as a gap between ribs is diagnosed, ultrasound transmission/reception cannot be carried out efficiently.

In addition, when the electrodes 105a and 106a are formed on the surfaces of the first and second acoustic matching layers 105 and 106, if a method is used such that the first and second acoustic matching layers 105 and 106 are exposed to a high temperature as in sputtering or the like, a deformation such as a warping is prone to occur in these matching layers 105 and 106. Therefore, there is a need for selecting a material that is not deformed so much even if it is exposed to a high temperature. As a result, a problem with higher cost has occurred.

BRIEF SUMMARY OF THE INVENTION

The present invention has been made in view of the circumstance described above. It is an object of the present invention to provide an ultrasound probe having a small portion that comes into contact with a subject, and moreover, achieving low cost.

According to an aspect of the present invention, there is provided an ultrasound probe comprising at least one acoustic matching layer between an acoustic lens and piezoelectric oscillators, wherein an electrode is arranged on a surface of a laminate element made of said at least one acoustic matching layer, the laminate element is interposed between the acoustic lens and the piezoelectric oscillator, and the piezoelectric oscillator and the electrode are electrically connected to each other.

According to another aspect of the present invention, there is provided an ultrasound probe which comprises: an acoustic lens; a piezoelectric oscillator including a first electrode and a second electrode; a laminate element laminated between the acoustic lens and the piezoelectric oscillator and including at least one acoustic matching layer; and a third electrode formed at least partly of a side face of the laminate element and a side face of the piezoelectric oscillator so as to be electrically connected to the first electrode and electrically insulated from the second electrode.

According to yet another aspect of the present invention, there is provided a method for manufacturing an ultrasound probe which comprises piezoelectric oscillators and an acoustic laminate element, the each piezoelectric oscillator including a first electrode and a second electrode and the acoustic laminate element being provided on the first electrode and including a plurality of acoustic matching layers, the method comprising: adhering a plurality of acoustic matching layer boards which are a material for said each acoustic matching layer, and have greater dimensions than those of the acoustic matching layer to form a material laminate element; reshaping the material laminate element in a required shape to form the acoustic laminate element; laminating the acoustic laminate element on the first electrode of the each piezoelectric oscillator; forming a third electrode on surfaces of the acoustic laminate element and the piezoelectric oscillators; and grinding at least part of the third electrode so that the third electrode is electrically connected to the first electrode and is electrically insulated from the second electrode.

According to yet another aspect of the present invention, there is provided a method for manufacturing an ultrasound probe that comprises an acoustic laminate element composed of a plurality of acoustic matching layers on an electrode of each piezoelectric oscillator, the method comprising: adhering a plurality of acoustic matching layer boards which are a material for said each acoustic matching layer, and have greater dimensions than those of the acoustic matching layer to form a material laminate element; reshaping the material laminate element in a required shape to form the acoustic laminate element; forming an electrode on a surface of the acoustic laminate element; and laminating the acoustic laminate element on the electrode of the each piezoelectric oscillator to electrically connect the electrode of the piezoelectric oscillator and an electrode of the acoustic laminate element to each other.

DETAILED DESCRIPTION OF THE INVENTION

First, a first embodiment of the present invention will be described with reference to FIGS. 1 and 2.

Figure 1:
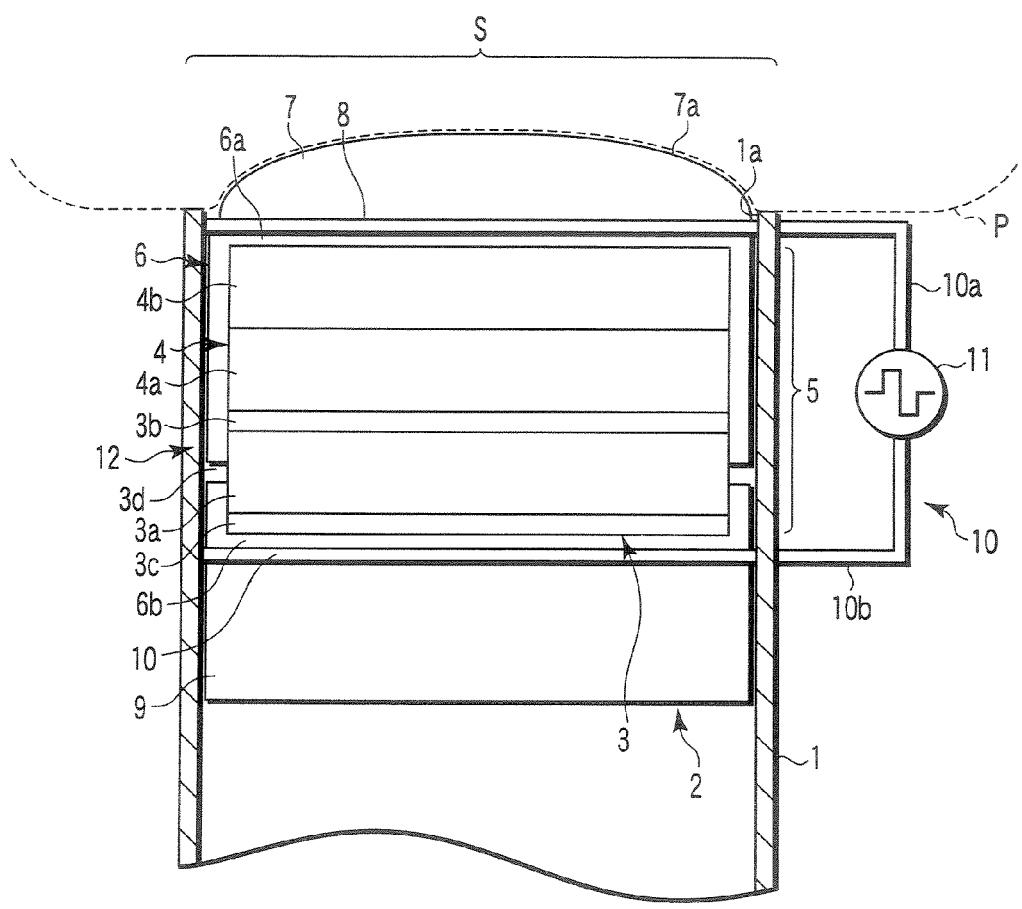
FIG. 1 is a schematic view showing an ultrasound probe according to a first embodiment of the present invention.

FIG. 1 is a schematic view showing an ultrasound probe according to the first embodiment of the present invention.

As shown in FIG. 1, the ultrasound probe according to the present invention has a casing 1 for an operator to grip. This casing 1 is formed in a rectangular cylinder shape, and an ultrasound transducer 2 is housed inside the casing.

The ultrasound transducer 2 has a plurality of piezoelectric oscillators 3 for transmitting and receiving an ultrasound. This each piezoelectric oscillator 3 is composed of: a flat rectangular parallelepiped shaped piezoelectric material 3a; a GND electrode (electrode) 3b formed on a face at the side of a subject P of the piezoelectric material 3a; and a signal electrode 3c formed on a face at the frontal side of the piezoelectric material 3a.

An acoustic matching layer 4 for matching acoustic impedances of the piezoelectric oscillator 3 and the subject P is provided on a face at the side of the subject P of the piezoelectric oscillator 3, i.e., on the GND electrode 3b. This acoustic matching layer 4 is made of a first acoustic matching layer (acoustic matching layer) 4a and a second acoustic matching layer (acoustic matching layer) 4b made of different materials, which gradually vary from the piezoelectric oscillator 3 toward the subject P. The acoustic matching layer 4 configures a transmitter/receiver laminate element 5 together with the piezoelectric oscillator 3.

While the acoustic matching layer 4 is configured as being two-layered in the present embodiment, the number of layers is not limited thereto. In addition, in the present embodiment, an insulation member is used as a material for each of the first and second acoustic matching layers 4a and 4b.

Further, although not shown in FIG. 1, this transmitter/receiver laminate element 5 is arrayed in a direction vertical to paper face, and ultrasound scanning can be executed for the subject P by controlling drive signals to be applied to the piezoelectric oscillators 3.

An electrode 6 made of a metal such as gold is formed at a portion excluding a ring shaped region 3d of a surface of the transmitter/receiver laminate element 5. This electrode 6 is mainly intended for drawing the GND electrode 3b of the piezoelectric oscillator 3 to the side of the subject P of the acoustic matching layer 4, and configures a transmitter/receiver unit 12 together with the transmitter/receiver laminate element 5. The ring shaped region 3d is provided in a ring shape all over four side faces of the piezoelectric material 3a, and an electrode 6 is separated into a GND side electrode 6a and a signal side electrode 6b. In this manner, the piezoelectric oscillator 3 is driven by applying a drive voltage to the GND side electrode 6a and the signal side electrode 6b. In the case where the first and second acoustic matching layers 4a and 4b each have electric conductivity, there is no need for forming the electrode 6 on the surface of the transmitter/receiver laminate element 5.

On a face at the side of the subject P of the transmitter/receiver unit 12, an acoustic lens 7 for improving ultrasound resolution is provided via a GND common electrode 8. This acoustic lens 7 protrudes to the side of the subject P from an aperture portion 1a formed on an end face at the side of the subject P of the casing 1, and a curved abutment portion 7a that comes into contact with the subject P is formed on a protrusive face of the lens.

As a material for the acoustic lens 7, there is used a silicone rubber or the like having acoustic impedance close to that of a living body. The GND common electrode 8 is provided so that a face at the side of the subject P of the transmitter/receiver laminate element 5 is completely covered, and a plurality of GND side electrodes 6a divided by arraying them are electrically connected in common.

When the abutment portion 7a of the acoustic lens 7 is applied to the subject P, an end face of the aperture portion 1a of the casing 1 also comes into contact with the subject P. Therefore, a portion that comes into contact with the subject P, i.e., the abutment portion 7a and the end face of the aperture portion 1a of the casing 1 are referred to as a subject's contact portion (biological contact portion) S.

On the face of the frontal side of the transmitter/receiver unit 12, a backing member 9 is provided via a signal substrate 10b (described later). This backing member 9 is intended for eliminating an unnecessary ultrasound by absorbing the ultrasounds having propagated to the frontal side from among the ultrasounds generated at the piezoelectric oscillator 3.

A flexible substrate 10 is arranged laterally of the transmitter/receiver unit 12. While this flexible substrate 10 is allocated in the casing 1, this substrate is shown laterally of the casing 1 for the sake of convenience.

The flexible substrate 10 comprises a GND substrate 10a and a signal substrate 10b. The GND substrate 10a has a GND wire (not shown), and the GND wire and the GND common electrode 8 are electrically connected to each other. The signal substrate 10b has a plurality of signal wiring patters (not shown), and these signal wiring patterns and a plurality of signal side electrodes 6b divided by arraying them are electrically connected to each other, respectively.

In this manner, a drive voltage from a pulser (not shown) of a control unit 11 is applied to the piezoelectric oscillator 3 via the GND side electrode 6a and the signal side electrode 6b, and then, a receive voltage from the piezoelectric oscillator 3 is received by a receiver (not shown) of the control unit 11 via the GND side electrode 6a and the signal side electrode 6b.

Now, a description will be given with respect to a process for manufacturing the ultrasound probe having the above configuration.

FIGS. 2A, 2B, 2C, 2D and 2E are process diagrams showing a process for manufacturing the ultrasound probe according to the present embodiment.

Figure 2A:
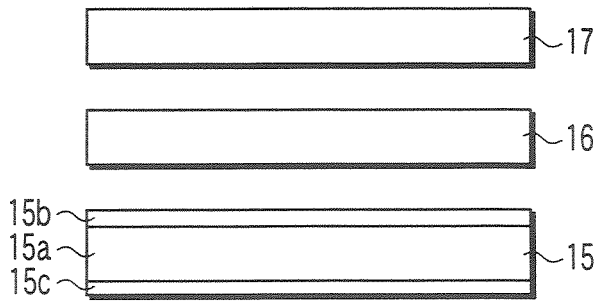
FIGS. 2A, 2B, 2C, 2D and 2E are process diagrams showing a process for manufacturing the ultrasound probe according to the first embodiment.

In the case of manufacturing the ultrasound probe by a method according to the present embodiment, as shown in FIG. 2A, first, there are prepared: a piezoelectric oscillator board 15 before diced, serving as a material for the piezoelectric oscillator 3; a first acoustic matching layer board (acoustic matching layer board) 16 before diced, serving as a material for the first acoustic matching layer 4a; and a second acoustic matching layer board (acoustic matching layer board) 17 before diced, serving as a material for the second acoustic matching layer 4b.

The piezoelectric oscillator board 15, the first acoustic matching layer board 16, and the second acoustic matching layer board 17 prepared here have greater dimensions than those of the piezoelectric oscillator 3, the first acoustic matching layer 4a, and the second acoustic matching layer 4b.

In addition, the piezoelectric oscillator board 15 is composed of: a piezoelectric material board 15a to become the piezoelectric material 3a by means of dicing; a first electrode 15b to become the GND electrode 3b by means of dicing; and a second electrode 15c to become the signal electrode 3c by means of dicing.

Figure 2B:
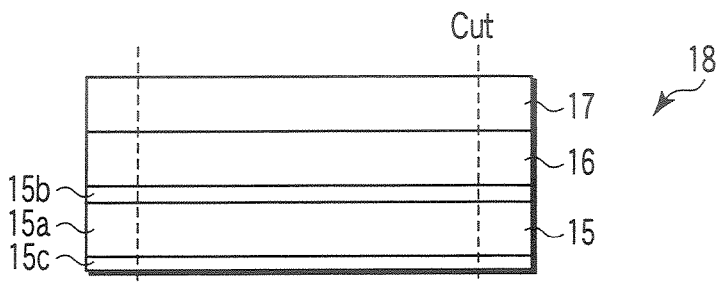
Figure 2C:
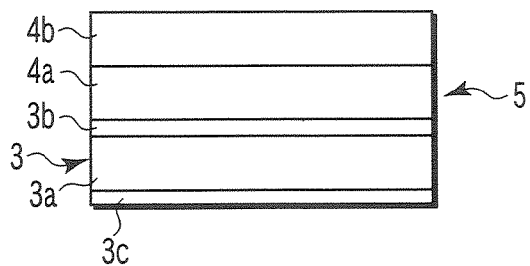
Figure 2D:
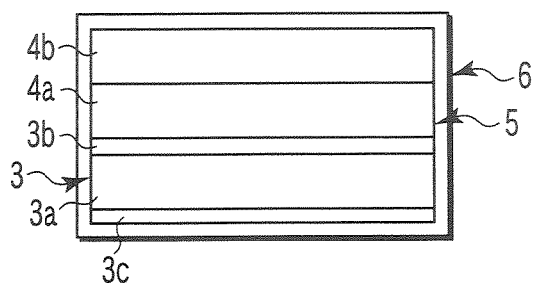
Figure 2E:
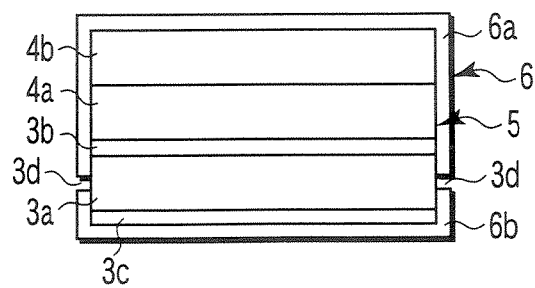

Next, as shown in FIG. 2B, these piezoelectric oscillator board 15, first acoustic matching layer board 16, and second acoustic matching layer board 17 are adhered by means of adhesive or the like, thereby forming a laminate board 18, and then, an outer periphery portion of this laminate board 18 is reshaped by means of dicing or the like. In this manner, as shown in FIG. 2C, the transmitter/receiver laminate element 5 having size and shape to be mounted on the ultrasound transducer 2 is completed.

Next, on the whole surface of the completed transmitter/receiver laminate element 5, an electrode 6 made of a metal such as gold is formed by means of sputtering or plating. While sputtering or plating is used as a method for forming the electrode 6 in the present embodiment, the method is not limited thereto.

Next, part of the electrode 6 formed on a side face of the piezoelectric material 3a is eliminated by means of dicing, and then, a ring shaped region 3d in which the electrode 6 does not exist is formed, the ring shaped region communicating with all of the four side faces of the piezoelectric material 3a. In this manner, the electrode 6 is separated into a GND side electrode 6a and a signal side electrode 6b, and then, the transmitter/receiver unit 12 is completed. While dicing is used to form the ring shaped region 3d in the present embodiment, the method for forming the region is not limited thereto. For example, before forming the electrode 6, a mask capable of preventing the adhering of a metal may be formed on a side face of the piezoelectric material 3a.

Next, a signal substrate 10b of the flexible substrate 10 and the backing member 9 are sequentially bonded on a face at the frontal side of the transmitter/receiver unit 12. Then, after the transmitter/receiver unit 12 has been arrayed by means of dicing, the GND common electrode 8 and the acoustic lens 7 are sequentially bonded on a face at the side of the subject P of the transmitter/receiver unit 12. In this manner, the ultrasound transducer 2 is completed.

According to the ultrasound probe configured as described previously, after there have been adhered to each other: the piezoelectric oscillator board 15 before diced, serving as a material for the piezoelectric oscillator 3; the first acoustic matching layer board 16 serving as a material for the first acoustic matching layer 4a; and the second acoustic matching layer board 17 serving as a material for the second acoustic matching layer 4b, their outer periphery portions are reshaped by means of dicing or the like, thereby forming the transmitter/receiver laminate element 5 having shape and dimensions to be mounted on the ultrasound transducer 2.

Therefore, when the transmitter/receiver laminate element 5 has been completed, the outer periphery portion of the piezoelectric oscillator 3, the outer periphery portion of the first acoustic matching layer 4a, and the outer periphery portion of the second acoustic matching layer 4b are just aligned to each other. That is, a displacement with respect to a direction crossing an axial line of the ultrasound transducer 2 hardly exists, thus making it possible to reduce a size of the casing 1 for housing the ultrasound transducer 2. As a result, a subject's contact portion S is reduced, and, even at a narrow portion such as a gap between ribs, efficient ultrasound transmission and receiving can be carried out.

Moreover, after the transmitter/receiver laminate element 5 has been completed, the electrode 6 is formed. That is, the electrode 6 is formed with respect to the transmitter/receiver laminate element 5 having certain thickness as compared with the first and second acoustic matching layers 4a and 4b.

Therefore, even in the case where a method for exposing a target to a high temperature such as sputtering has been used as a method for forming the electrode 6, a warping or the like is unlikely to occur in the first and second acoustic matching layers 4a and 4b. As a result, materials for the first and second acoustic matching layers 4a and 4b can be selected more flexibly, making it possible to reduce a material cost.

In addition, the GND side electrode 6a is formed on a surface of the completed transmitter/receiver laminate element 5. Therefore, the GND electrode 3b and the GND common electrode 8 can be electrically connected to each other without applying limitation to the materials for the first acoustic matching layer 4a and the second acoustic matching layer 4b. As a result, the materials for the first and second acoustic matching layers 4a and 4b can be selected more flexibly, making it possible to reduce a material cost.

In the present embodiment, as shown in FIG. 2, one transmitter/receiver laminate element 5 is fabricated using each of the piezoelectric oscillator board 15, the first acoustic matching layer board 16, and the second acoustic matching layer board 17, whereas a plurality of transmitter/receiver laminate elements 5 can be fabricated using a comparatively large piezoelectric oscillator board 15, a first acoustic matching layer board 16, and a second acoustic matching layer board 17.

For example, eight sector type probe oscillators having an effective aperture of 12 mm×20 mm can be fabricated using a 50 mm×50 mm piezoelectric oscillator board, a first acoustic matching board, and a second acoustic matching board.

A second embodiment of the present invention will be described with reference to FIG. 3. A description of the same constituent elements and functions as the foregoing embodiment is omitted here.

Figure 3:
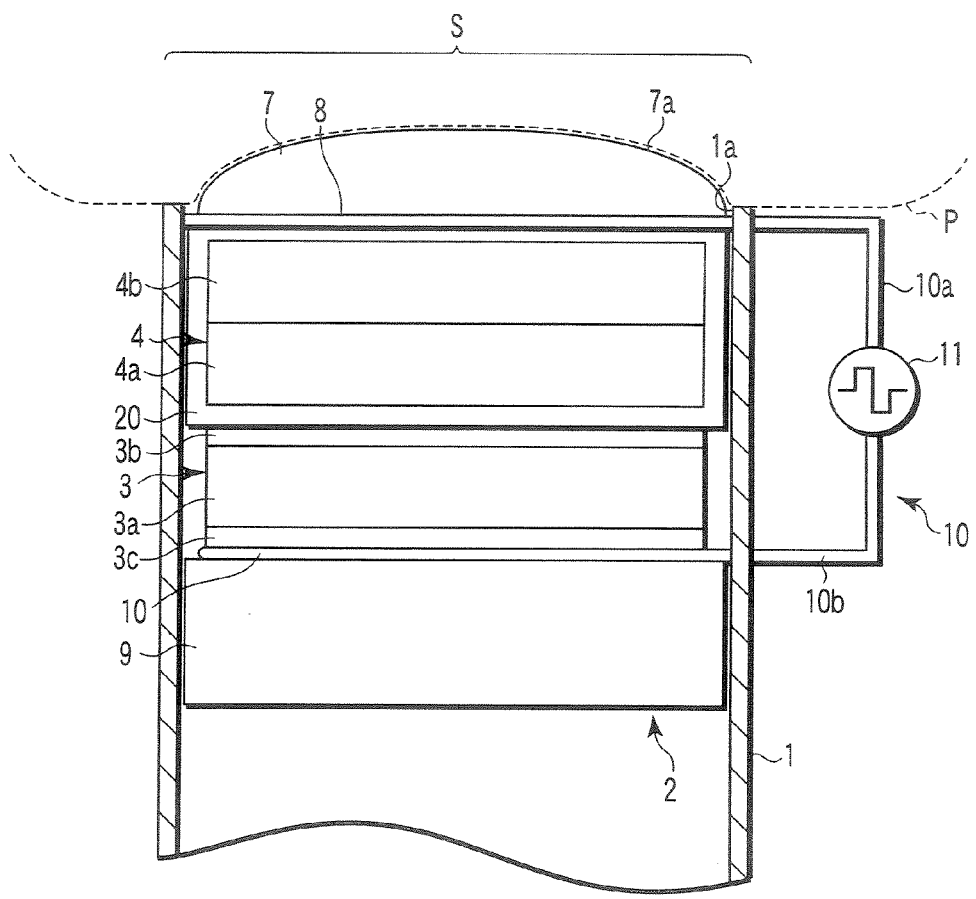
FIG. 3 is a schematic view showing an ultrasound probe according to a second embodiment of the present invention.
Figure 4:
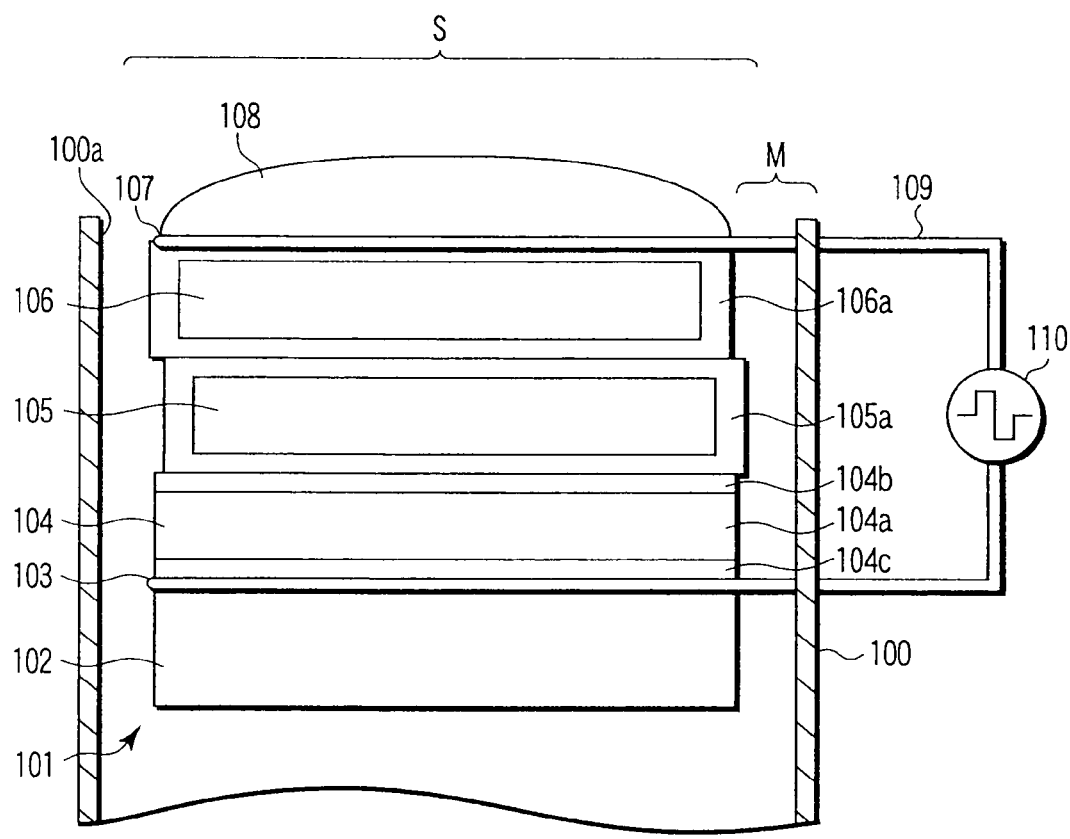
FIG. 4 is a schematic view showing a conventional ultrasound probe.

FIG. 3 is a schematic view showing an ultrasound probe according to a second embodiment of the present invention.

As shown in FIG. 3, in the ultrasound probe according to the present embodiment, an electrode 20 made of a metal such as gold is formed only on the whole surface of an acoustic matching layer (acoustic laminate element) 4. This electrode 20 is intended, as in the first embodiment, to draw a GND electrode 3b of a piezoelectric oscillator 3 to the side of a subject P of the acoustic matching layer 4, and configures an acoustic matching unit 29 together with the acoustic matching layer 4.

Now, a description will be given with respect to a process for manufacturing the ultrasound probe configured as described previously.

In the case of manufacturing the ultrasound probe according to the present embodiment, first, a first acoustic matching layer board before diced, serving as a material for a first acoustic matching layer 4a; and a second acoustic matching layer board before diced, serving as a material for a second acoustic matching layer 4b are adhered to each other by means of adhesive, and their outer periphery portions are reshaped by means of dicing or the like. In this manner, the acoustic matching layer 4 having size and shape to be mounted on an ultrasound transducer 2 is formed.

Next, on the whole surface of the acoustic matching layer 4, the electrode 20 made of a metal such as gold is formed by means of sputtering or plating. In this manner, the acoustic matching unit 29 is completed. While sputtering or plating is used as a method for forming the electrode 20 in the present embodiment, the method is not limited thereto.

Next, the acoustic matching unit 29 is bonded with the GND electrode 3b of the piezoelectric oscillator 3 so that the first acoustic matching layer 4a is located at the frontal side and the second acoustic matching layer 4b is located at the side of the subject P. Then, a signal substrate 10b of a flexible substrate 10 and a backing member 9 are sequentially bonded with a signal electrode 3c of the piezoelectric oscillator 3; a transmitter/receiver unit 12 is arrayed by means of dicing; and then, a GND common electrode 8 and an acoustic lens 7 are sequentially bonded on a face at the side of the subject P of the transmitter/receiver unit 12. Then, the ultrasound transducer 2 is completed.

In the ultrasound probe according to the present embodiment, after a first acoustic matching layer board 25 serving as a material for the first acoustic matching layer 4a has been adhered to the second acoustic matching layer board 26 serving as a material for a second acoustic matching layer 4b, their outer periphery portions are reshaped by means of dicing or the like, thereby forming the acoustic matching layer 4 having size and dimensions to be mounted on the ultrasound transducer 2.

Therefore, when the acoustic matching layer 4 has been completed, the outer periphery portion of the first acoustic matching layer 4a and the outer periphery portion of the second acoustic matching layer 4b are just aligned to each other. That is, a displacement with respect to a direction crossing an axial line of the ultrasound transducer 2 hardly exists, thus making it possible to reduce a size of the casing 1 for housing the ultrasound transducer 2. As a result, a subject's contact portion S is reduced, and, even in a narrow region such as a gap between ribs, efficient ultrasound transmission and receiving can be carried out.

In addition, the electrode 20 is formed on the whole surface of the completed acoustic matching layer 4. Therefore, even if an electrically conductive member is not used for the first acoustic matching layer 4a and the second acoustic matching layer 4b, the GND electrode 3b of the piezoelectric oscillator 3 and the GND common electrode 8 can be electrically connected to each other. As a result, materials for the first and second acoustic matching layers 4a and 4b can be selected more flexibly, making it possible to reduce a material cost.

Moreover, after the acoustic matching layer 4 has been competed, the electrode 20 is formed. That is, the electrode 20 is formed with respect to the acoustic matching layer 4 having certain thickness as compared with the first and second acoustic matching layers 4a and 4b.

Therefore, even in the case where a method for exposing a target to a high temperature such as sputtering has been used as a method for forming the electrode 20, a warping or the like is unlikely to occur in the first and second acoustic matching layers 4a and 4b. As a result, materials for the first and second acoustic matching layers 4a and 4b can be selected more flexibly, making it possible to reduce a material cost.

The present invention is not limited to the embodiments described previously. At the stage of carrying out the invention, the present invention can be embodied by modifying constituent elements without departing from the spirit of the invention. In addition, a variety of inventions can be formed by using a proper combination of a plurality of constituent elements disclosed in the embodiments described previously. For example, some constituent elements may be deleted from all the constituent elements presented in the embodiments. Further, different constituent elements according to the different embodiments may be properly combined with each other.

Specifically, while the acoustic matching layer 4 is composed of the first and second acoustic matching layer boards 16 and 17 in the present embodiment, this layer is not limited thereto. For example, a filler is mixed with adhesive, the resulting mixture is formed in a planar shape, and, thickness grinding is applied after dry curing, whereby the above matching layer may be configured.

In addition, each of the embodiments described above exemplifies a case in which a laminate element is made of two acoustic matching layers. However, the technical idea of the present invention can be applied without being limited thereto, even in the case where the laminate element is made of three or more acoustic matching layers or even in the case where the laminate element has a single acoustic matching layer.

What is claimed is:

1. An ultrasound probe comprising:
   at least one acoustic matching layer between an acoustic lens and piezoelectric oscillators, wherein
   an electrode is formed over an entirety of at least three side faces of a laminate element made of said at least one acoustic matching layer, the laminate element being interposed between the acoustic lens and the piezoelectric oscillator, and the piezoelectric oscillator and the electrode being electrically connected to each other.

2. The ultrasound probe according to claim 1, wherein, of two end faces of the laminate element perpendicular to an ultrasound transmission direction of the piezoelectric oscillator, an electrode-drawing substrate is connected to an end face distant from the piezoelectric oscillator.

3. The ultrasound probe according to claim 1, wherein the electrode is arranged on side faces of the laminate element parallel to the ultrasound transmission direction of the piezoelectric oscillator.

4. The ultrasound probe according to claim 1, wherein the electrode is integrally formed so as to cover entire side faces of the laminate element and at least a part of a side face of the piezoelectric oscillator.

5. The ultrasound probe according to claim 1, wherein the electrode is integrally formed so as to cover entire surfaces of the laminate element.

6. An ultrasound probe comprising:
   an acoustic lens;
   a piezoelectric oscillator including a first electrode and a second electrode;
   a laminate element laminated between the acoustic lens and the piezoelectric oscillator and including at least one acoustic matching layer; and
   a third electrode formed over an entirety of at least three side faces of the laminate element and a side face of the piezoelectric oscillator so as to be electrically connected to the first electrode and electrically insulated from the second electrode.

7. The ultrasound probe according to claim 6, wherein the third electrode is integrally formed so as to cover side faces of the acoustic laminate element, an acoustic-lens-side surface of the acoustic laminate element, and part of a side face of the piezoelectric oscillator.

8. The ultrasound probe according to claim 6, wherein the laminate element is laminated at the first electrode side, and the first electrode is an electrode for ground connection.

9. An ultrasound probe comprising:
   an acoustic lens;
   a piezoelectric oscillator including a first electrode and a second electrode;
   a laminate element laminated between the acoustic lens and the piezoelectric oscillator and including at least one acoustic matching layer; and
   a third electrode formed over an entirety of at least three side faces of the laminate element and electrically connected to the first electrode.

10. The ultrasound probe according to claim 9, wherein the laminate element is laminated at the first electrode side, and the first electrode is an electrode for ground connection.

11. The ultrasound probe according to claim 1, wherein the laminate element includes four side faces and two end faces, and
the electrode is formed over an entirety of all four side faces and over an entirety of one end face of the laminate element.

12. The ultrasound probe according to claim 1, wherein the electrode is formed over side faces of the laminate element by sputtering or plating.

* * * * *